(12) United States Patent
Cerniway

(10) Patent No.: US 6,358,049 B1
(45) Date of Patent: Mar. 19, 2002

(54) ENDODONTIC TOOL LENGTH GAUGE

(76) Inventor: Leon A. Cerniway, 398 Pudding Ridge, South Mills, NC (US) 27976

( * ) Notice: Subject to any disclaimer, the term of this patent is extended or adjusted under 35 U.S.C. 154(b) by 0 days.

(21) Appl. No.: 09/778,815

(22) Filed: Feb. 8, 2001

Related U.S. Application Data

(60) Provisional application No. 60/180,961, filed on Feb. 8, 2000.

(51) Int. Cl.$^7$ .............................................. A61C 19/04
(52) U.S. Cl. ........................... 433/72; 433/102; 33/513; 33/626
(58) Field of Search ........................... 433/72, 75, 102, 433/77; 33/513, 626

(56) References Cited

U.S. PATENT DOCUMENTS

| | | |
|---|---|---|
| 3,964,170 A | 6/1976 | Zdarsky |
| 4,028,810 A | 6/1977 | Vice |
| 4,182,040 A | 1/1980 | Bechtold, Jr. |
| 4,557,690 A | 12/1985 | Randin |
| 5,827,060 A | 10/1998 | Zdarsky |
| 6,160,264 A | 12/2000 | Rebiere |

*Primary Examiner*—Nicholas D. Lucchesi
(74) *Attorney, Agent, or Firm*—Andrew M. Hill

(57) ABSTRACT

A gauge serving as a jig to adjust exposed length of endodontic files with respect to respective encircling resilient stops which prevent overpenetration into a root canal of a patient. The gauge has a body bearing four parallel, coplanar tracks for slidably receiving an equal number of slides. Each slide has a plurality of spaced apart steps enabling endodontic files to be adjusted to differing operating lengths, and a thumbscrew which secures the slide in place within its track. The thumbscrews are arranged to establish a two discrete levels of friction, the first enabling fine adjustment and the second locking the slide in place. A retaining barrier formed in the body has a plurality of openings for each track, thereby being able to receive and make multiple adjustments to several files when the latter are placed against any one slide. Measurement indicia are optionally borne near one or more tracks, for setting the slides to correspond to radiographic lengths of a patient's root canals. The retaining barrier projects above the upper surface of the slides, thereby enabling an endodontic ruler to be placed against the gauge to make the radiographic length setting. Slides are provided in two or more groups, each group differing in spacing characteristics of the steps.

17 Claims, 7 Drawing Sheets

ENDODONTIC TOOL LENGTH GAUGE

REFERENCE TO RELATED APPLICATION

This application claims priority benefit of Provisional Patent Application Ser. No. 60/180,961, filed Feb. 8, 2000.

BACKGROUND OF THE INVENTION

1. Field of the Invention

The present invention relates to geometric dental tools and more particularly to an instrument serving as a jig to adjust exposed lengths of endodontic tools such as files with respect to encircling stops placed along the length of a file to prevent over-penetration into a root canal of a patient.

2. Description of the Prior Art

When the nerve of a tooth dies or other injury occurs to pulp tissue of a tooth, potentially necrotic and infected tissue must be removed. The canal containing pulp tissue is enlarged and sterilized, and then filled with an inert material. Removal of pulp tissue and enlargement of the canal are performed by drilling a hole through the top of the tooth, then reaming out the canal of each root of the tooth. Reaming of each canal is performed usually in several progressive steps each corresponding to file diameter or file length or both. Each step in file length typically requires a series of endodontic files of progressively greater diameter than the prior file used. For example, a single root canal procedure may require four files of varying diameter for the widest enlargement of a canal nearest the tooth crown, and progressively fewer sets of files as work approaches the apex or tip of the root. The progression culminates in a single file utilized at the apex of the root.

The procedure requires establishment of a fixed point of reference, called the datum point, on the tooth itself. Each canal to be treated requires a datum point that is within the diameter of the stop which encircles each file. The distance from the datum point to the tip end, or apex of the root, is established. This is referred to as the "radiographic tolength". From this information, the dimensions of progressive file lengths are determined according to the particular surgical technique chosen by the clinical practitioner. Because of the number of files of differing diameter and lengths required, it is not uncommon for a treatment of a single root to include more than sixty file length settings. This number is simply repeated for each canal in a multi-root tooth.

The several sets of endodontic files for each succeeding increment of file length are prepared with great precision to correspond to the length of each section of each root canal. Lengths are determined by radiological images obtained by X-rays. Generally torroidal or disc-like resilient stops are placed over each endodontic file which will be utilized in the procedure. These stops limit maximal penetration of the file into the canal. Precision of placement of a stop on its associated file is of great importance in limiting the exposed portion of the files. The precision required and the large number of settings present a significant risk of error, and multiply time required to perform the procedure. Accordingly, the prior art has proposed gauges for enabling precise placement of a stop on its associated file.

U.S. Pat. No. 4,182,040 issued to Edmund C. Bechtold, Jr. on Jan. 8, 1980, is representative of cylindrical file length gauges. By contrast, the present invention avoids cylindrical configuration.

U.S. Pat. No. 4,028,810, issued to Bobby C. Vice on Jun. 14, 1977, shows a flat or planar file length gauge. The design of Vice lacks a plurality of slidably adjustable positioning members held in a plurality of tracks, as seen in the present invention.

U.S. Pat. No. 3,964,170, issued to Eduard Zdarsky on Jun. 22, 1976, describes a flat file gauge. However, there are no slidably adjustable positioning members in the device of Zdarsky, as there are in the present invention.

U.S. Pat. No. 4,557,690, issued to Jean-Claude Randin on Dec. 10, 1985, and U.S. Pat. No. 5,827,060, issued to Constantin Zdarsky on Oct. 27, 1998, both illustrate devices for handling the torroidal or disc-like stops for endodontic files. Neither of these two patents has slidably adjustable positioning members, as seen in the present invention.

None of the above inventions and patents, taken either singly or in combination, is seen to describe the instant invention as claimed.

SUMMARY OF THE INVENTION

The present invention provides a convenient instrument for adjusting operational lengths of endodontic files with respect to respective encircling stops preventing overpenetration into a root canal of a patient. The novel instrument or gauge is able to set all necessary operational lengths for all files required for performing root canal procedures on up to four root canals at once. The relatively spread out configuration of the novel gauge provides a number of benefits. One is that when all operational length settings are made to the novel tool prior to performing an endodontic procedure, a dental practitioner can more readily determine and remember the stage to which the procedure has progressed at any point in time.

A second benefit is that a selected endodontic file can be readily inserted into its appropriate place within the novel gauge, set to the proper operational length, and subsequently removed for use. The practitioner is not unduly burdened by having to manipulate the file to adjust it to constantly changing operational length settings, as is required in many prior art devices. Still another benefit is that the present invention is more effectively sterilized in autoclaves, compared to cylindrical devices, due to its spread out planar configuration.

The novel gauge comprises a flat base provided with an anvil or retaining barrier, and four tracks for receiving slidable members, hereinafter called slides, which can be positioned within the base to adjust operational lengths of endodontic files. The retaining barrier serves as a measuring point at which stops are positioned on files being adjusted for operational length. Each slide is configured to present the number and altitude of steps dictated by the particular technique chosen for the procedure, thereby being able to adjust length of all files for one root canal with one manual an adjustment.

The four tracks enable the device to set up all file lengths required for up to four root canals, which corresponds to the maximum number of roots of the overwhelming majority of teeth. Thus one length setting per track can be utilized to prepare all needed endodontic files for any one tooth having up to four roots, and to display the settings in a readily accessible, organized manner. The settings thus displayed visually presents the logical order of each step in file lengths for each root to be treated. The invention anticipates a separate set of slides for each of the known and generally practiced techniques for performing root canal procedures, and additional techniques which may be developed in the future.

Each slide is secured in a selected position relative to the base by a thumbscrew. In one embodiment, the thumbscrew serves as a handle for maneuvering the slide along its track. In a preferred embodiment, the thumbscrew has a combination of compressible O-ring, spacer ring, and washer that selectively establishes two levels of frictional engagement of the slide as the thumbscrew is progressively tightened. The first level of friction prevents unintended, spontaneous dislodging of the slide during a final tightening sequence, but enables the slide to be moved by manual force prior to final tightening. The second level of friction locks the slide in a selected operational position on the base so that not even manual force can dislodge it. The slides are therefore secured within the base in two discrete increments of mobility.

Measurement indicia may be optionally provided for adjusting slides to precise positions on the base relative to the retaining barrier. As an alternative to the measurement indicia, or in addition thereto, an upwardly projecting flange is provided on each slide. The flange facilitates use of an endodontic ruler in measuring the distance from the retaining barrier to a predetermined point on the slide, thereby establishing the radiographic length to which the slide is to be adjusted. Thus two forms of measurement of tools may be provided.

Accordingly, it is one object of the invention to provide a length gauge for adjusting exposed length of endodontic tools with respect to stops, which gauge readily displays, makes accessible, and visually organizes all operational length settings for all files which will be used to treat one tooth.

It is another object of the invention that the gauge be of a configuration enabling effective sterilizing.

It is a further object of the invention to provide means to make file length adjustments for many different techniques for performing root canal treatments.

Still another object of the invention is to secure slides within the base in increments of mobility along the length of their associated tracks.

An additional object of the invention is to facilitate and enable measurement of distances displayed by the jig which distances will correspond to the desired exposed lengths of the tools.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
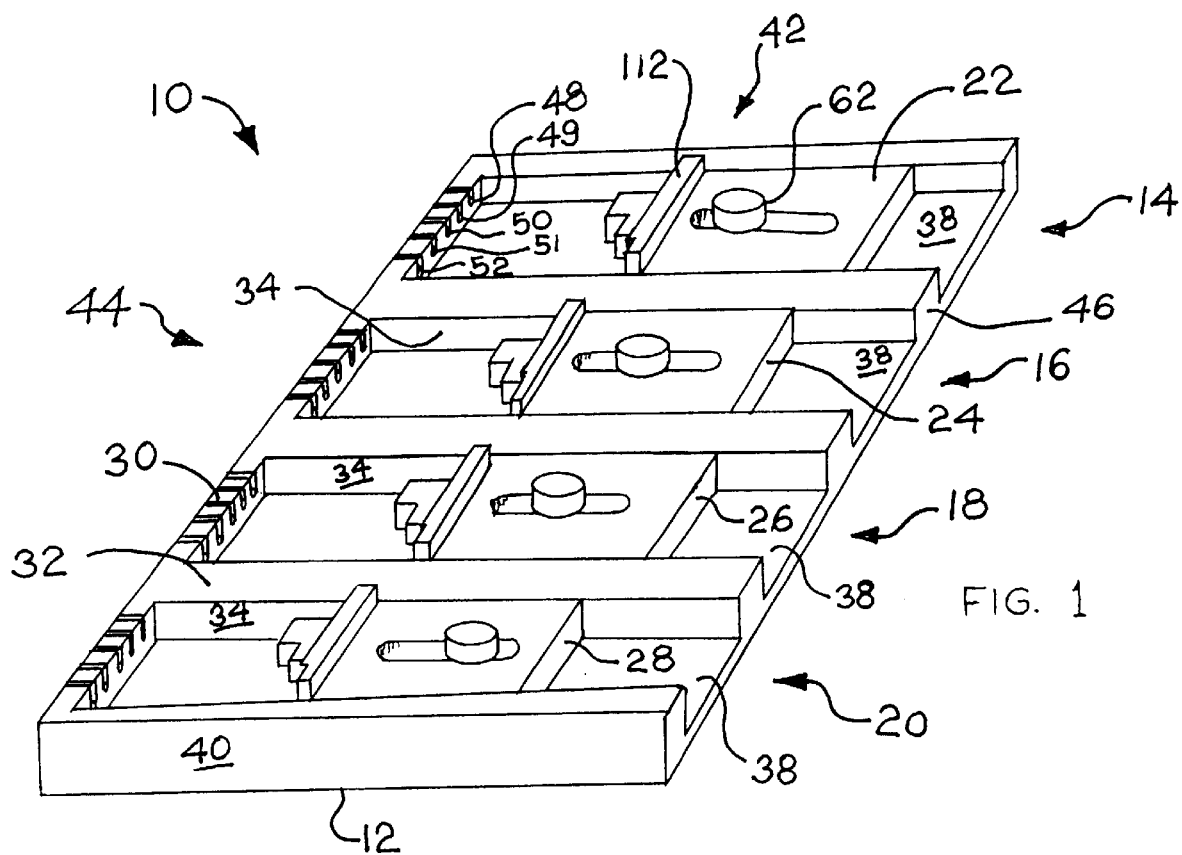
FIG. 1 is a perspective view of an embodiment of the invention.
Figure 2:
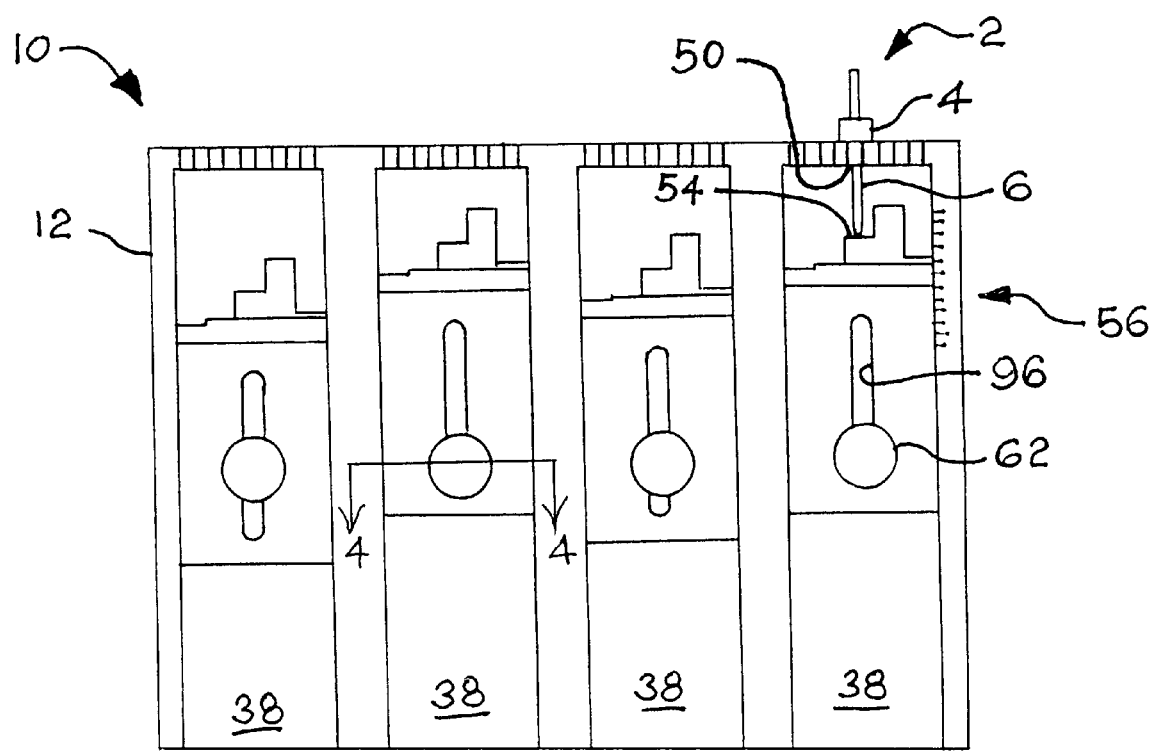
FIG. 2 is an environmental, top plan view of the device of FIG. 1.

FIG. 1 of the drawings shows gauge 10 for selectively positioning stops along the shaft of an endodontic file (see FIG. 2). Gauge 10 comprises a base 12 in which are formed four coplanar, parallel tracks 14, 16, 18, 20. A plurality of slidable members or slides 22, 24, 26, 28 which are dimensioned and configured to be slidably disposed within tracks 14, 16, 18, and 20 are shown installed. Base 12 has a retaining barrier 30 spanning tracks 14, 16, 18, 20. Base 12 has an upper surface 32 common to retaining barrier 30 and to side walls 34 of tracks 14, 16, 18, 20. The function of barrier 30 will be described hereinafter.

The bottom of base 12, as depicted in FIG. 1, is formed by a floor 38 (see also FIG. 2) which extends continuously from side 40 to respective opposing side 42, and from proximal side 44 to respective opposing distal side 46. Designation of side 44 as proximal and of side 46 as distal are merely for semantic convenience. The proximal side is that into which files are inserted into retaining barrier 30. The term will also be applied for convenience to tracks 14, 16, 18, 20, and refers to that end of tracks 14, 16, 18, 20 proximate retaining barrier 30.

Apart from being a structural member, floor 38 closes each track 14, 16, 18, or 20 at the bottom thereof. This both assists in guiding and constraining slides 22, 24, 26, 28 to move only longitudinally within associated tracks 14, 16, 18, 20 which are dimensioned and configured to accomplish this, and also obstructs contaminants (not shown) from impinging from below upon endodontic files (see FIG. 2) held within base 12.

The use of gauge 10 is illustrated in FIG. 2. An endodontic file 2 is shown held in base 12. File 2 is passed through one of five openings 48, 49, 50, 51, 52 formed in retaining barrier 30 at track 14. Openings 48, 49, 50, 51, 52 are preferably slots which are open from above so that a file may be laid in each one prior to sliding the file into contact with its associated slide. Openings 48, 49, 50, 51, 52 are each dimensioned and configured to receive therein one endodontic file such that all endodontic files (only one file 2 is shown) inserted within openings 48, 49, 50, 51, 52 are in coplanar relation to one another. A rubbery, generally torroidal or disc-like stop 4 has been placed in encircling relation to the shaft of file 2 prior to insertion of file 2 into opening 50. File 2 has been passed through opening 50 until its distal end contacts a step 54 formed on slide 22.

Slide 22 has a stepped surface facing retaining barrier 30 at its proximal end (that being the end facing retaining barrier 30) and an opposed distal end. The stepped surface is disposed to occupy track 14, and to move selectively towards and away from the proximal end of track 14 when slide 22 traverses track 14. The stepped surface has five flat steps 54, 55, 57, 58, 60 (see FIG. 5). Each step 54, 55, 57, 58, or 60 is spaced apart from the distal end of track 14 by a distance interval different from that by which every other step 54, 55, 57, 58, or 60 is spaced apart from the distal end of track 14.

In the depiction of FIG. 2, slide 22 has been moved to a selected position within track 14 such that exposed length 6 of file 2 corresponds to a measurement derived from the radiographic length, which is established by X-ray or equivalent images (not shown). Positioning of slide 22 is precisely accomplished by moving slide 22 to appropriate registry with measurement indicia 56 disposed upon upper surface 32 of base 12 proximate and along track 14. Indicia 56 enables visual confirmation of exposed length of each endodontic file retained within retaining barrier 30. A similar goal is achieved by the use of an endodontic ruler, as explained hereinafter. Slide 22 bears a suitable index or reference mark (not shown) for registry with indicia 56. Stop 4 is prevented from moving in tandem with file 2 as file 2 is pushed through opening 50, stop 4 thereby moving to an adjusted position along the shaft of file 2 as facilitated by retaining barrier 30. Alternatively stated, retaining barrier 30 causes stop 4 which has been placed in encircling relation on the shaft of endodontic file 2 to slide along the shaft when the shaft is advanced through opening 50. When exposed length 6 of file 2 touches step 54, position of stop 4 on file 2 has been adjusted to the desired distance. File 2 is now ready for use.

Other files (not shown), also for use on the same root canal, will be similarly adjusted, using other openings 48, 49, 51, or 52, of retaining barrier 30, and other steps 55, 57, 58, or 60 of slide 22. Another file (not shown) is passed through an opening 48, 49, 51, or 52 until it contacts its associated step 55, 57, 58, or 60 of slide 22. The length of the exposed portion of file 2 and other files adjusted using slide 22 is predetermined once slide 22 has been adjusted to the appropriate position in accordance with the radiographic length of the canal. The procedure for positioning the stops of the subsequent files is the same as that employed for file 2. Files associated with any one slide may obviously be adjusted in any desired order.

Each track 14, 16, 18, or 20 preferably has height, width of magnitude greater than that of the height, and length of magnitude greater than that of the width. This relationship causes gauge 10 to be generally planar, apart from nominal and structural thickness of its components, so that all of the files are held in an accessible, visible parallel, coplanar array.

It will be appreciated that because track 14 and slide 22 are generally similar in function to respective tracks 16, 18, and 20 and slides 24, 26, and 28, description of track 14 and slide 22 will therefore be understood to apply as well to tracks 16, 18, and 20 and to slides 24, 26, and 28. The only significant difference is in dimensions and proportions among the various slides, as will be further explained hereinafter. In a similar vein, retaining barrier 30 has five openings (not indicated by individual reference numerals) for each one of tracks 16, 18, 20, as well as for track 14.

In operation, each track 14, 16, 18, or 20 is assigned to a canal in the tooth to be treated. Each track 14, 16, 18, or 20 can, with a single adjustment to its associated slide 22, 24, 26, or 28, therefore set up to five operational file lengths as dictated by the chosen endodontic technique. Each operational length is a predetermined variance from the radiographic length of the individual canal.

All tracks 14, 16, 18, 20 face upwardly when base 12 is oriented horizontally, with floor 38 facing downwardly. Therefore, all five file lengths established by slides 22, 24, 26, 28 after adjustment are exposed to view from above.

Once positioned as desired, and prior to inserting files into openings 48, 49, 50, 51, 52, slide 22 is secured within base 12 by turning a setscrew which preferably is a thumbscrew 62. It will be understood that slides 24, 26, 28 each have an equivalent thumbscrew.

Figure 3:
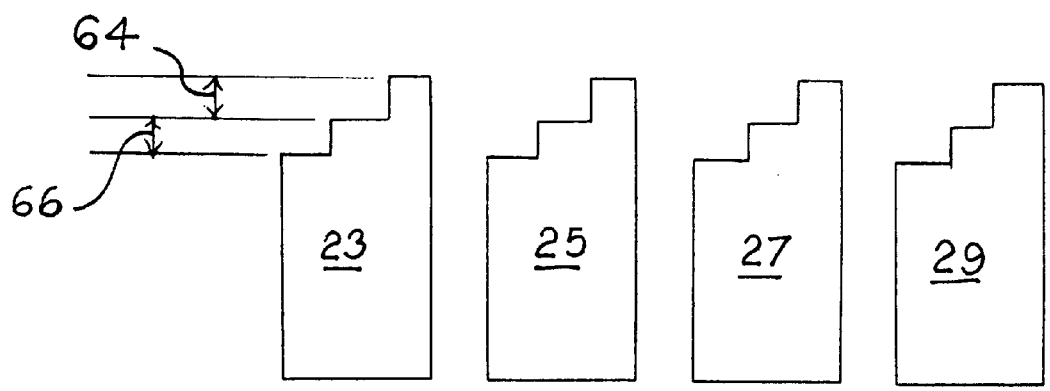
FIG. 3 is a diagrammatic plan view of slides generally corresponding to four members seen along the center of FIG. 1.
Figure 3:
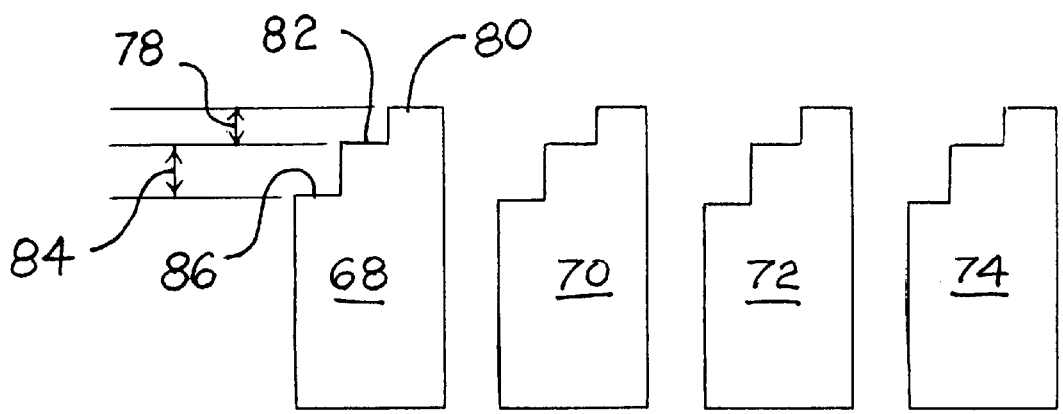
Figure 3:
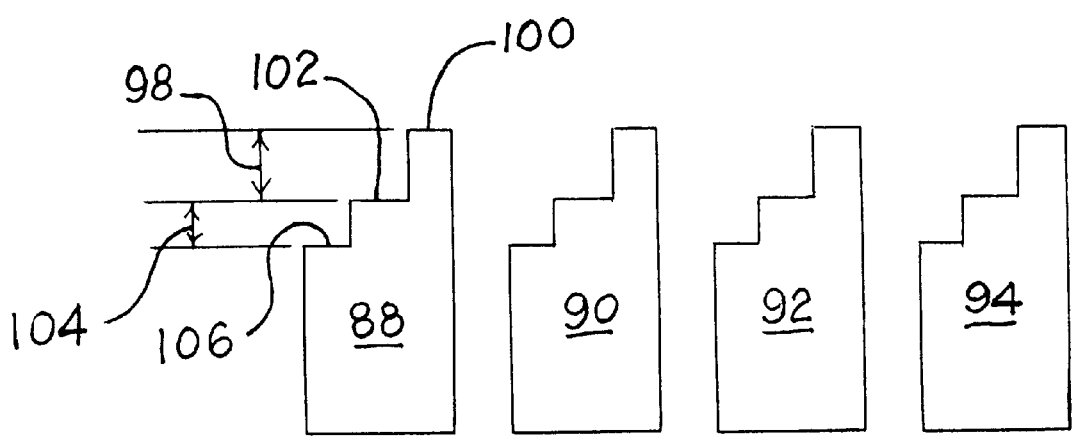

Differences among the dimensions and proportions of the various slides will now be described, with reference to FIG. 3. FIG. 3 illustrates a second embodiment of the invention wherein slides 23, 25, 27, 29 each have other than five steps. The number of steps arbitrarily selected for purpose of illustration is three. Variations among the slides are selected to conform to teachings of different clinical techniques for root canal procedures. FIG. 3 is diagrammatic in that it shows only the profile or silhouette of each slide, omitting other features described elsewhere herein. It will be understood that the various slides of FIG. 3 include necessary features required for operability but which are It will be seen that distance intervals 64, 66 by which steps of slides 23, 25, 27, 29 of a first group of slides are spaced apart from one another are constant or similar distance intervals. This is not the only possible relationship. A second group comprising slides 68, 70, 72, 74 has a distance interval 78 separating a step 80 for establishing the shortest exposed file length from an intermediate step 82 which is smaller than a distance interval 84 separating intermediate step 82 from step 86. It will be understood that although steps 80, 82, 86 are shown only on slide 68, slide 68 and steps 80, 82, 86 are representative of slides 70, 72, 74.

Figure 4A:
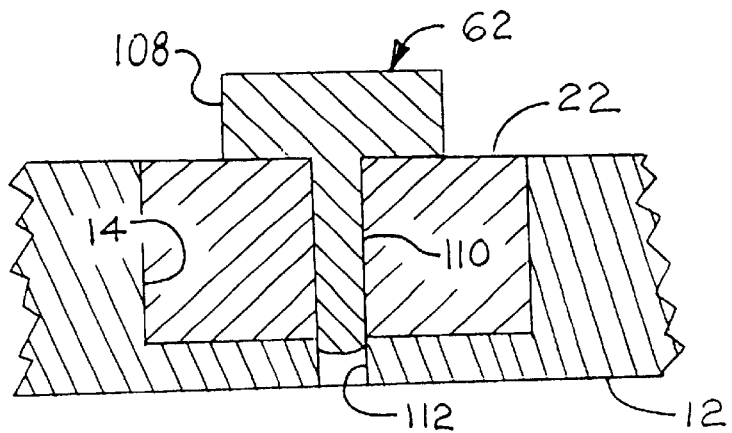
FIG. 4A is an enlarged end cross sectional detail view taken along line 4—4 of FIG. 2.

FIG. 4A illustrates one method of securement of slide 22 within track 14. Thumbscrew 62 is seen to comprise an enlarged head 108 which enables grasping by finger and a threaded shank 110 which threaded shank 110 engages a threaded hole 112 formed in slide 22. Shank 110 passes through a slot 96 (see FIG. 5) formed in slide 22. Thumbscrew 62 is turned to thread to and engage hole 112. Continuing to turn thumbscrew 62 will immobilize slide 22 within its associated track 14.

Figure 4B:
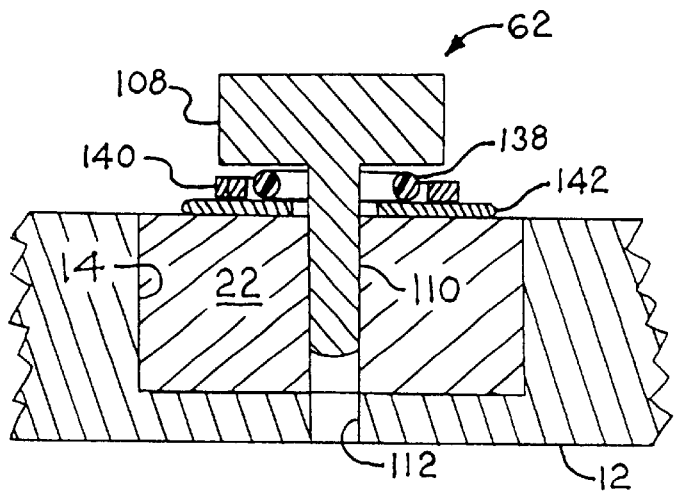
FIG. 4B is similar to FIG. 4A, but shows an alternative embodiment thereof.

FIG. 4B shows a modification to the embodiment of FIG. 4A, wherein apparatus providing two discrete levels of friction as thumbscrew 62 is tightened. The added apparatus is similar in structure and function to corresponding apparatus shown in and described with reference to FIGS. 7 and 8. The embodiment of FIG. 4B is preferred over the embodiments of FIGS. 4A and 7.

Figure 4C:
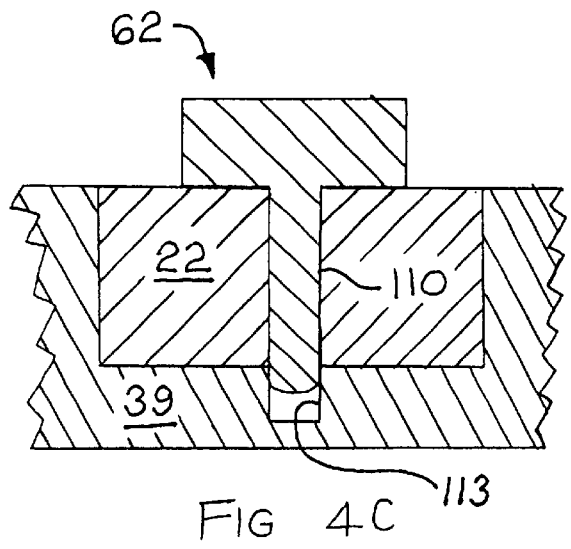
FIG. 4C is an enlarged end cross sectional detail view generally corresponding to the bottom of FIG. 4A, but shows an alternative embodiment thereof.

FIG. 4C shows a modification to the embodiment of FIG. 4A. In FIG. 4C, floor 39 of a base (not shown in its entirety) which is otherwise comparable to body 12 of FIG. 1 is continuous, thereby closing the bottom of threaded hole 113 which receives threaded shank 110 of thumbscrew 62. Of course, the modification shown in FIG. 4C could be applied to the embodiment shown in FIG. 4B in order to provide the latter with a continuous floor.

Figure 5:
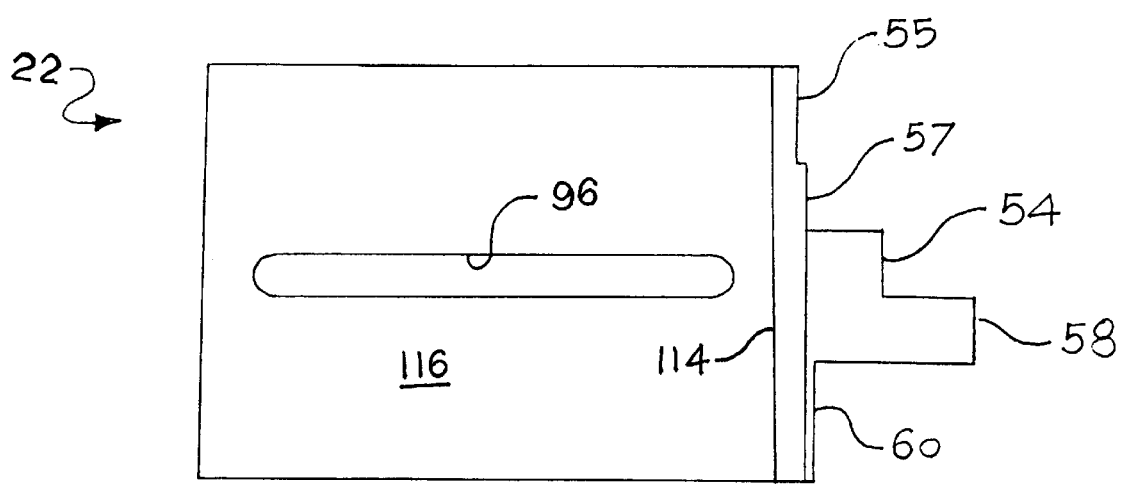
FIG. 5 an enlarged top plan detail view of one of the slides depicted along the center of FIG. 1.
Figure 6:
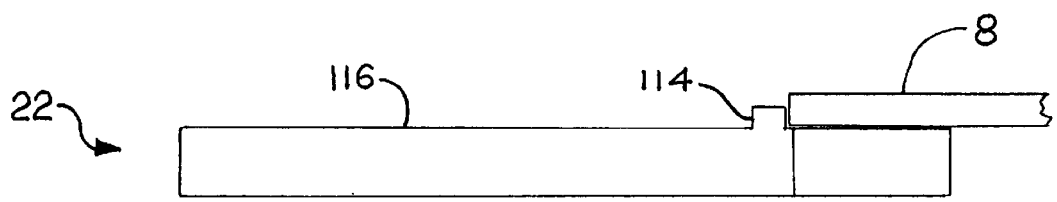
FIG. 6 is an enlarged environmental side elevational detail view of the slide of FIG. 5, showing an endodontic ruler in place for making measurements.

In FIGS. 5 and 6, it will be seen that slide 22 has a ridge or flange 114 which projects upwardly above upper surface 116 of slide 122. Flange 114 serves as a stop against which an endodontic ruler 8 may be placed for making measurements in adjusting position of slide 22 within base 12 (see FIG. 1). This is a preferred embodiment which renders indicia 56 (see FIG. 2) unnecessary, although both may be provided if desired. It will be seen from examining FIG. 5 that step 55 is recessed behind the forward surface of flange 114. Step 57 is coincident or coplanar with the forward surface of flange 114. Steps 54, 58, 60 are located forwardly of the forward surface of flange 114. While step 60 is shown lower than step 58, steps 55, 57, 54, 58, and 60 are considered to be generally arranged in ascending order with respect to distance to the retaining barrier. The order shown generally corresponds to the order required in the treatment procedure, thus facilitating ease of use, although other orders could be employed.

Figure 7:
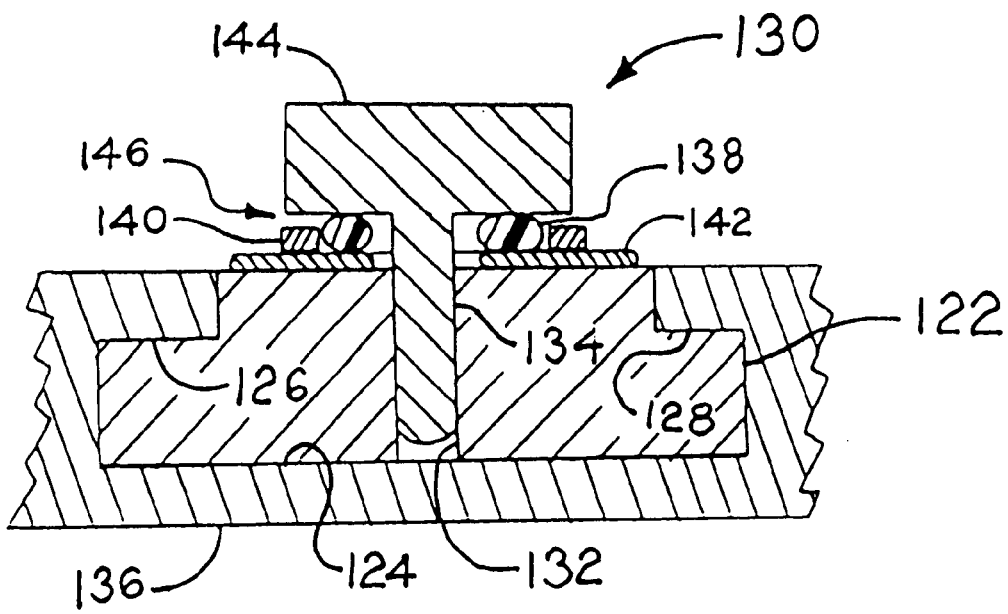
FIG. 7 is an enlarged end cross sectional detail view of an alternative embodiment of the structure shown in FIG. 4.

FIG. 7 shows an alternative embodiment of the invention wherein a slide 122 is formed such that it cannot be lowered into track 124 and therefore cannot be lost by moving upwardly. Each one of the several tracks of the embodiment of FIG. 7 is dimensioned and configured to guide and constrain its associated slide to move only longitudinally within the track. To this end, the body forming track 124 has two wings 126, 128 which interfere with dovetailing or cooperating portions of slide 122.

Slide 122 is inserted into track 124 from the distal end thereof, and may be withdrawn only from the distal end of track 124. Slide 122 is secured in place by tightening thumbscrew 130 into a threaded hole 132 formed in slide 122, until the bottom of threaded shank 134 of thumbscrew 130 contacts floor 136 of the body forming track 124. Continued tightening of thumbscrew 130 forces slide 122 upwardly into interference with wings 126, 128. This contact secures slide 122 in place within track 124.

Figure 8:
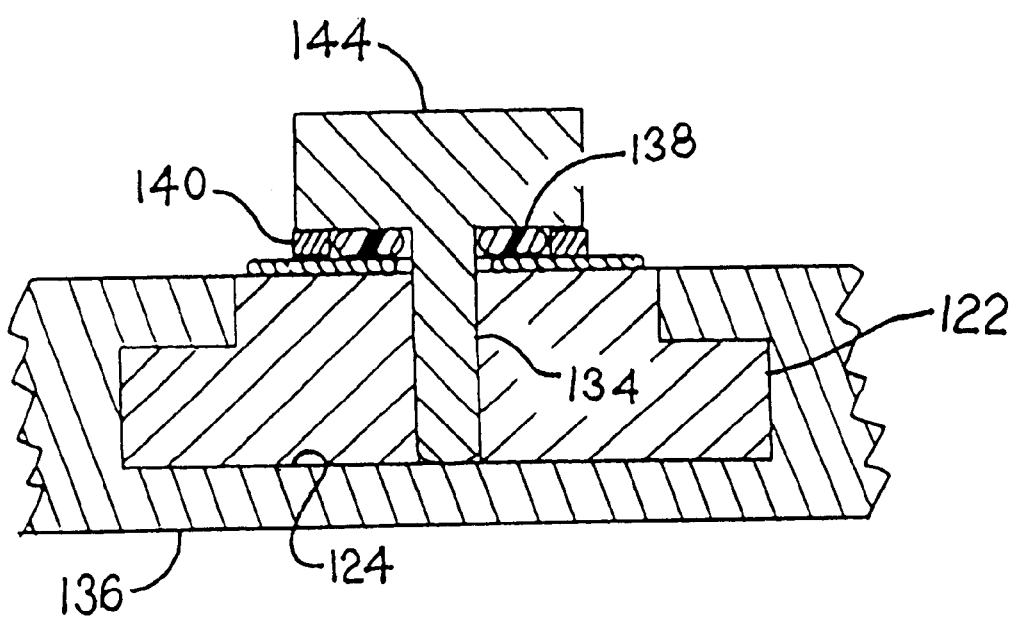
FIG. 8 is similar to FIG. 7, but shows a progressive degree of tightening of the thumbscrew shown therein.

FIGS. 7 and 8 show a further feature wherein frictional engagement of thumbscrew 130 progressively increases in discrete increments providing tactile indication of degree of securement of slide 122 within track 124. A resilient O-ring 138 encircles shank 134. In turn, a rigid keeper 140 encircles O-ring 138. A washer 142 separates keeper 140 and O-ring 138 from the upper surface of slide 122. As thumbscrew 130 is threaded into slide 122, the lower surface of enlarged head 144 of thumbscrew 130 contacts and slightly compresses O-ring 138. The degree of contact establishes a first level of friction between enlarged head 144 and slide 122 when thumbscrew 130 is only partially threaded into threaded hole 132. The first level of friction is preferably sufficient to secure slide 122 within track 124 against spontaneous movement, while enabling slide 122 to be moved by manual force.

It will be seen that a gap 146 remains between enlarged head 144 and keeper 140 in FIG. 7. As thumbscrew 130 continues to be turned, as shown in FIG. 8, the lower surface of enlarged head 144 not only further compresses O-ring 138 but also engages keeper 140. It will be seen that gap 146 which was present in FIG. 7 has now disappeared. Also, the bottom of threaded shank 134 now engages floor 136. Contact of head 144 with slide 122 establishes a second level of friction between enlarged head 144 and slide 122 when the bottom surface of shank 134 seats against the upper surface of floor 136. Preferably, the second level of friction is sufficient to secure slide 122 within track 124 against displacement by manual pressure.

The advantage of the two levels of friction is that the first level of friction enables a person to move slide 122 along track 124 to a selected position from which it will not be spontaneously dislodged. Frictional resistance also assists in moving slide 122 in very small increments of distance, thereby making very precise, accurate positioning possible.

After slide 122 has been adjusted to a precise selected position, resultant additional frictional resistance assures that careless handling and incidental impacts will not disturb accuracy of the adjustment.

In a preferred embodiment, the feature providing two levels of friction may be incorporated into the embodiment of FIG. 4A. Although the embodiment of FIGS. 7 and 8 retain slide 122 against loss in the upward direction, wings 126, 128 may perhaps reduce effectiveness of sterilization when placing the base in an autoclave (not shown). Therefore, the embodiment of slide 22 of FIG. 4 is preferred over the embodiment of slide 122 of FIGS. 7 and 8.

The number of openings formed in the retaining barrier at each track generally corresponds to the number of steps on a slide. But such characterization should not be construed to preclude having a number of openings which is more or less than the number of steps in the slide provided. For example, the retaining barrier could have five openings for each slide, while the slides utilized therewith could have only three steps. Hence, this would allow a slide having either three steps or five steps to use the same base, namely one having five openings for each slide. Moreover, a slide having more steps than openings provided therefore could be employed, in which case not all steps would be utilized. Of course, the number of openings and slide steps could be matched for the sake of simplicity. The desired implementation is to provide a corresponding number of openings and steps to facilitate adjustment of the number of files utilized in accordance with a corresponding canal and selected procedure.

The present invention is susceptible to variations which may be introduced thereto without departing from the inventive concept. Elements set forth in the singular may be replaced by plural elements to the same effect. Any of the variations of alternative embodiments may be combined as desired. For example, the number of steps of any slide may be varied to suit. The different groups illustrated in FIG. 3 may vary in any and all of the characteristics shown herein. Openings 48, 49, 50, 51, 52 could be holes rather than slots as depicted.

It is to be understood that the number of steps of any slide, the order in which the steps of a slide occur, and the relative heights of the steps of a slide in relation to the retaining barrier will vary according to variations among differing root canal treatment techniques.

There is no requirement that the tracks for the slides or the openings formed in a retaining barrier literally be coplanar. Rather, they are preferably arranged such that the length settings are longitudinally exposed to view in one common direction. It would be possible to rearrange the tracks as seen in FIGS. 9 and 10.

Figure 9:
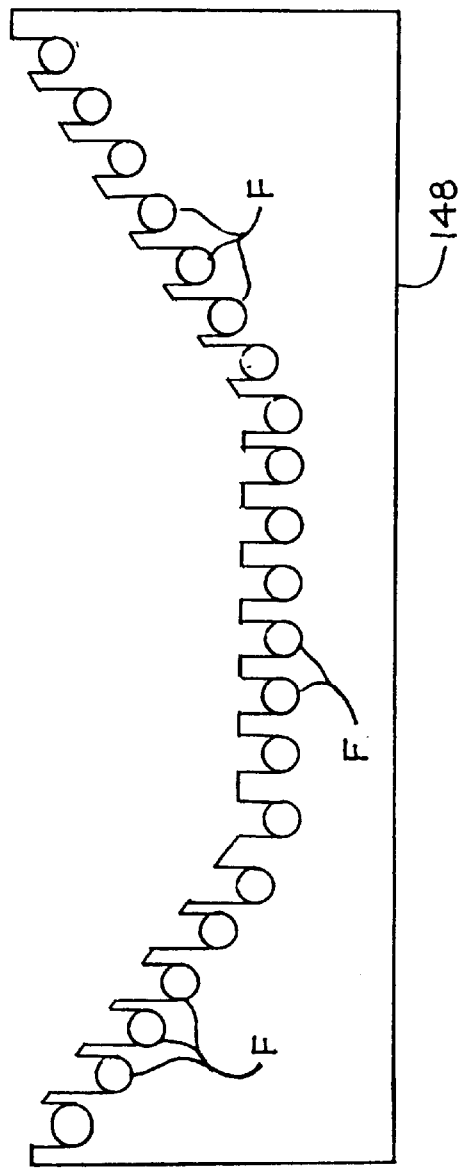
FIG. 9 is an enlarged diagrammatic, end elevational view is of a further embodiment of the invention.
Figure 10:
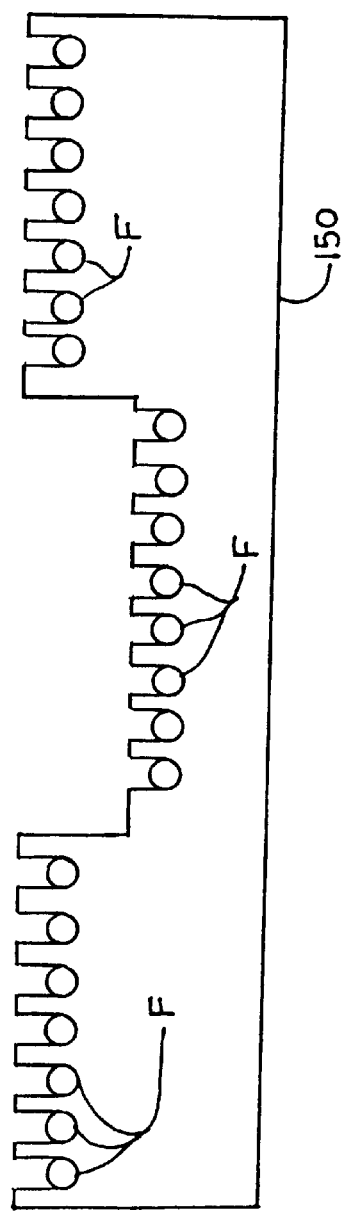
FIG. 10 is an enlarged diagrammatic, end elevational view of a still further embodiment of the invention.

In FIG. 9, a base 148 is arranged so that endodontic files F are all parallel and exposed from above. However, they are not literally coplanar. FIG. 10 shows a second arrangement wherein a base 150 is arranged such that endodontic files F are parallel and exposed from above. Files F are exposed to view from a common direction, that being from above, so that they are readily visually organized and accessible without being coplanar. It will be recognized that FIGS. 9 and 10 are only diagrammatic in nature, and omit retaining barriers, slides, and tracks for brevity. The omitted components would be present in any embodiment of the invention having configuration of the embodiments of FIGS. 9 or 10.

It is to be understood that the present invention is not limited to the embodiments described above, but encompasses any and all embodiments within the scope of the following claims.

I claim:

1. A gauge for selectively positioning stops along the shaft of endodontic files, comprising:

a base having formed therein a plurality of tracks each having a proximal end and a distal end, a floor disposed on one side of all of said tracks, and a retaining barrier disposed proximate said proximal end of said tracks, wherein said retaining barrier has a plurality of openings each dimensioned and configured to receive therein an endodontic file, wherein all endodontic files disposed within said openings of said retaining barrier are aligned in coplanar relation to one another; and a plurality of slides which are dimensioned and configured to be independently slidably disposed and securable within said tracks, wherein each one of said slides has an end surface disposed to face said retaining barrier, wherein said retaining barrier is disposed to cause a stop placed in encircling relation on the shaft of an endodontic file to slide along the shaft when the shaft is advanced through a said opening of said retaining barrier, and wherein said tracks are arranged to display endodontic files such that the endodontic files are longitudinally exposed to view from a common direction.

2. The gauge according to claim 1, wherein each one of said tracks is dimensioned and configured to guide and constrain its associated said slide to move only longitudinally within said track.

3. The gauge according to claim 1, wherein each said slide has a proximal end bearing a stepped surface and an opposed distal end, said stepped surface is disposed to occupy one said track and to move selectively towards and away from said proximal end of said track when said slide traverses said track, and said stepped surface has a plurality of flat steps each of which is spaced apart from said distal end by a distance interval different from that of every other said flat step.

4. The gauge according to claim 3, wherein said retaining barrier has openings formed at each track, the number of which said openings corresponding to the number of said steps of each said slide.

5. The gauge according to claim 3, wherein each said slide has a plurality of said steps generally arranged in ascending order of distance by which each said step is spaced apart from said proximal end of said track.

6. The gauge according to claim 5, wherein said steps of each one said slide are spaced apart from one another by a constant distance interval.

7. The gauge according to claim 5, wherein said steps of each one said slide are spaced apart from one another by different distance intervals.

8. The gauge according to claim 1, wherein said tracks are parallel to and disposed in coplanar relation to one another, and each said track has height, width of magnitude greater than that of said height, and length of magnitude greater than that of said width.

9. The gauge according to claim 1, wherein all of said tracks face upwardly, when said base is oriented horizontally and when said floor faces downwardly, thereby exposing all endodontic file settings to simultaneous view.

10. The gauge according to claim 1, wherein said base has measurement indicia disposed along at least one of said tracks, for enabling visual confirmation of length settings established for each endodontic file inserted through a said retaining barrier.

11. The gauge according to claim 1, wherein said floor extends continuously from every side of said base to every respective opposing side, thereby closing each said track at the bottom thereof and obstructing contaminants from impinging from below upon endodontic files disposed within said base.

12. The gauge according to claim 1, wherein each said slide has a setscrew disposed to engage said floor of its associated said track and to immobilize said slide within its associated said track when said setscrew is tightened.

13. The gauge according to claim 12, wherein each said setscrew is a thumbscrew having an enlarged head enabling grasping by finger.

14. The gauge according to claim 13, further comprising a first friction element disposed to establish a first level of friction between said enlarged head and said slide when said thumbscrew is partially threaded towards said floor of said base, and a second friction element disposed to establish a second, greater level of friction between said enlarged head and said slide when said thumbscrew is seated, wherein said first level of friction secures said slide within said track against spontaneous movement and enables said slide to be moved by manual pressure, and said second, greater level of friction secures said slide within said track against manual pressure.

15. The gauge according to claim 1, wherein said plurality of slides includes at least two groups of slides, wherein the number of slides within each said group is at least the number of said tracks, and wherein characteristics regarding spacing apart of said steps of each slide of one group of slides differs from characteristics regarding spacing apart of said steps of each slide of every other group of slides.

16. The gauge according to claim 1, wherein each said slide has an upper surface and a flange projecting upwardly above said upper surface, serving as a stop against which an endodontic ruler may be placed for making measurements.

17. The gauge according to claim 1, wherein said openings are slots open from above.

* * * * *